(12) United States Patent
Fink et al.

(10) Patent No.: US 7,605,160 B2
(45) Date of Patent: *Oct. 20, 2009

(54) PYRROLOTRIAZINE KINASE INHIBITORS

(75) Inventors: Brian E. Fink, Yardley, PA (US); Ping Chen, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/835,469

(22) Filed: Aug. 8, 2007

(65) Prior Publication Data

US 2008/0058337 A1 Mar. 6, 2008

Related U.S. Application Data

(60) Provisional application No. 60/821,835, filed on Aug. 9, 2006.

(51) Int. Cl.
| | |
|---|---|
| C07D 487/04 | (2006.01) |
| C07D 403/12 | (2006.01) |
| C07D 403/14 | (2006.01) |
| A61K 31/53 | (2006.01) |
| A61P 19/02 | (2006.01) |
| A61P 35/00 | (2006.01) |

(52) U.S. Cl. ...................... 514/243; 544/183
(58) Field of Classification Search ............... 544/183, 544/243, 283; 514/243
See application file for complete search history.

(56) References Cited

U.S. PATENT DOCUMENTS

| | | | |
|---|---|---|---|
| 6,670,357 B2 | 12/2003 | Leftheris et al. | |
| 6,869,952 B2 | 3/2005 | Bhide et al. | |
| 6,982,265 B1 | 1/2006 | Hunt et al. | |
| 2006/0084650 A1 | 4/2006 | Dong et al. | |

FOREIGN PATENT DOCUMENTS

WO WO 00/71129 11/2000

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys.vol. 58(3): 932-940, 2004.*
Fabbro et al. Pharmacology & therapeutics 93, 79-98, 2002.*

* cited by examiner

*Primary Examiner*—Venkataraman Balasubramanian
(74) *Attorney, Agent, or Firm*—Elliott Korsen

(57) ABSTRACT

The present invention provides compounds of formula I

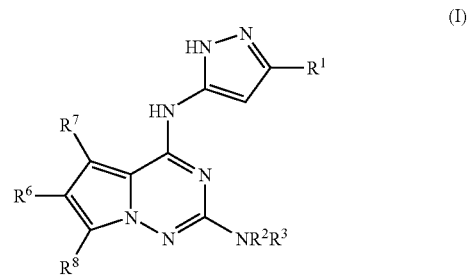

and pharmaceutically acceptable salts thereof.

The formula I compounds inhibit tyrosine kinase activity of Trk receptors such as TrkA, TrkB and TrkC thereby making them useful as antiproliferative agents for the treatment of cancer and other diseases.

11 Claims, No Drawings

PYRROLOTRIAZINE KINASE INHIBITORS

RELATED APPLICATION

This application claims the benefit of U.S. Provisional Application No. 60/821,835, filed Aug. 9, 2006, incorporated herein by reference in its entirety.

FIELD OF THE INVENTION

This invention relates to novel pyrrolotriazine compounds that are useful as anti-cancer agents. This invention also relates to a method of using the compounds in the treatment of proliferative diseases and to pharmaceutical compositions containing the compounds.

BACKGROUND OF THE INVENTION

Tropomysosin Related Kinases (Trk) are a family of receptor tyrosine kinases composed of three family members, TrkA, TrkB and TrkC. The Trks bind with high affinity to, and mediate the signal transduction induced by the Neurotrophin family of ligands whose prototype members are Nerve Growth Factor (NGF), Brain-Derived Neurotrophic Factor (BDNF), Neurotrophin-3, -4 and -5 (NT-4, NT-4 and NT-5). In addition, a co-receptor lacking enzymatic activity, p75, has been identified which binds all neurotrophines (NTs) with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. In addition to these developmental consequences of Trk signaling, the subversion of this receptor and its signaling pathway in certain malignancies has also been documented. Of particular note are reports of aberrant expression of NGF and TrkA receptor kinase are implicated in the development and progression of human prostatic carcinoma and pancreatic ductal adrenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuroectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. In addition, profound or significantly attenuated reduction of bone pain caused by prostate cancer metastasis has recently been achieved by utilization of an anti-NGF antibody. Overall, the oncogenic properties of Trk signaling in multiple tumor types makes the modulation of the Trk receptor signaling a potentially attractive therapeutic intervention point in different malignancies.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. In general, RTKs are activated by ligand-induced oligomerization and tyrosine autophosphorylation of specific intracellular substrates such as PLCγ, PI3 kinase, ras, and raf/MEK/Erk1. Tyrosine kinase activity is an absolute requirement for signal transduction through this class of receptor.

The Trk family of RTKs is frequently expressed in lung, breast, pancreatic and prostate cancers as well as in certain type of acute myelogenous leukemia and congenital fibrosarcoma. The tyrosine kinase activity of Trk is believed to promote the unregulated activation of cell proliferation machinery. It is believed that inhibitors of either TrkA, TrkB or TrkC, kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies.

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I

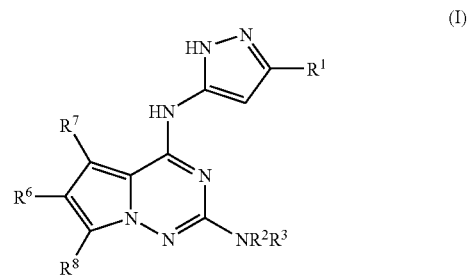

(I)

wherein the symbols have the following meanings and are, for each occurrence, independently selected:

$R^1$ is alkyl, substituted alkyl, cycloalkyl, substituted cycloalkyl, aryl, substituted aryl or —CONR$^4$R$^5$;

$R^2$ is hydrogen or $C_1$-$C_4$ alkyl;

$R^3$ is hydrogen, alkyl, substituted alkyl, cycloalkyl, substituted cycloalkyl, aryl, substituted aryl,

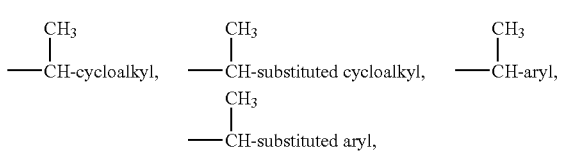

heteroaryl, substituted aryl, heteroaryl, substituted heteroaryl, heterocyclyl, substituted heterocyclyl, —CONHR$^4$, —CONHSO$_2$R$^4$, —(CH$_2$)$_n$-aryl, —(CH$_2$)$_n$-substituted aryl, —(CH$_2$)$_n$-heteroaryl, —(CH$_2$)$_n$-substituted heteroaryl, —(CHR$^4$)$_n$CONHalkyl, —(CHR$^4$)$_n$CONHsubstituted aryl, —(CHR$^4$)$_n$CONH heteroaryl, —(CHR$^4$)$_n$CONHsubstituted heteroaryl, —(CHR$^4$)$_n$CONH(CH$_2$)$_n$—OH, —(CH$_2$)$_2$(CH$_2$)$_n$—OH, —(CH$_2$)$_2$(CH$_2$)$_n$—NH$_2$ or —(CH$_2$)$_2$(CH$_2$)$_n$—S-alkyl, two of which may be attached to the same ring carbon atom provided that the resultant compound is chemically stable;

R$^4$ and R$^5$ are hydrogen, C$_1$-C$_4$ alkyl or phenyl;

R$^6$ and R$^7$ are hydrogen, C$_1$-C$_4$ alkyl, halogen, cyano, amino or substituted amino;

R$^8$ is hydrogen, C$_1$-C$_6$ alkyl, C$_1$-C$_6$ alkenyl, C$_1$-C$_6$ alkynyl, C$_3$-C$_8$ cycloalkyl, C$_1$-C$_5$ arylalkyl or C$_4$-C$_8$ heterocyclyl with at least one atom on the ring selected from a nitrogen or oxygen atom, and each of said R$^8$ groups optionally substituted with 1 to 3 groups selected from the group consisting of —OH, OR$^9$, —NH$_2$, —NR$^9$R$^{10}$, —CONHR$^9$, —OCONHR$^9$, —CONHSO$_2$R$^9$, —NHCONHR$^9$, —SR$^9$, —S(=O)R$^9$, —SO$_2$R$^9$ and —SO$_2$NR$^9$R$^{10}$;

R$^9$ is C$_1$-C$_6$ alkyl, C$_3$-C$_6$ cycloalkyl, an optionally substituted aryl or heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

R$^{10}$ is hydrogen, halogen, C$_1$-C$_6$ alkyl, C$_3$-C$_6$ cycloalkyl or C$_1$-C$_6$ alkoxy;

n is 0, 1, 2, 3 or 4;

or a pharmaceutically acceptable salt, tautomer or stereoisomer thereof.

In another embodiment, the invention comprises a compound of formula II

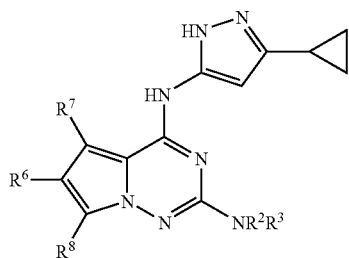

(II)

wherein:

R$^2$ is hydrogen or C$_1$-C$_4$ alkyl;

R$^3$ is hydrogen, alkyl, substituted alkyl, cycloalkyl, substituted cycloalkyl, aryl, substituted aryl,

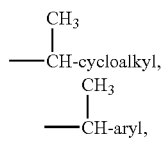

heteroaryl, substituted heteroaryl, heterocyclyl, substituted heterocyclyl, —CONHR$^4$, —CONHSO$_2$R$^4$, —(CH$_2$)$_n$-aryl, —(CH$_2$)$_n$-substituted aryl, —(CH$_2$)$_n$-heteroaryl, —(CH$_2$)$_n$-substituted heteroaryl, —(CHR$^4$)$_n$CONHalkyl, —(CHR$^4$)$_n$CONHsubstituted aryl, —(CHR$^4$)$_n$CONH heteroaryl, —(CHR$^4$)$_n$CONHsubstituted heteroaryl, —(CHR$^4$)$_n$CONH(CH$_2$)$_n$—OH, —(CH$_2$)$_2$(CH$_2$)$_n$—OH, —(CH$_2$)$_2$(CH$_2$)$_n$—NH$_2$ or —(CH$_2$)$_2$(CH$_2$)$_n$—S-alkyl, two of which may be attached to the same ring carbon atom provided that the resultant compound is chemically stable;

R$^4$ is hydrogen, C$_1$-C$_4$ alkyl or phenyl;

R$^6$ and R$^7$ are independently hydrogen, C$_1$-C$_4$ alkyl, halogen, cyano, amino or substituted amino;

R$^8$ is hydrogen, C$_1$-C$_6$ alkyl, C$_1$-C$_6$ alkenyl, C$_1$-C$_6$ alkynyl, C$_3$-C$_8$ cycloalkyl, C$_1$-C$_5$ arylalkyl or C$_4$-C$_8$ heterocyclyl with at least one atom on the ring selected from a nitrogen or oxygen atom, and each of said R$^8$ groups is optionally substituted with 1 to 3 groups selected from the group consisting of —OH, OR$^9$, —NH$_2$, —NR$^9$R$^{10}$, —CONHR$^9$, —OCONHR$^9$, —CONHSO$_2$R$^9$, —NHCONHR$^9$, —SR$^9$, —S(=O)R$^9$, —SO$_2$R$^9$ and —SO$_2$NR$^9$R$^{10}$;

R$^9$ is C$_1$-C$_6$ alkyl, C$_3$-C$_6$ cycloalkyl, an optionally substituted aryl or heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

R$^{10}$ is hydrogen, halogen, C$_1$-C$_6$ alkyl, C$_3$-C$_6$ cycloalkyl or C$_1$-C$_6$ alkoxy;

n is 0, 1, 2, 3 or 4;

or a pharmaceutically acceptable salt, tautomer or stereoisomer thereof.

In another embodiment, the invention comprises a compound of formula III

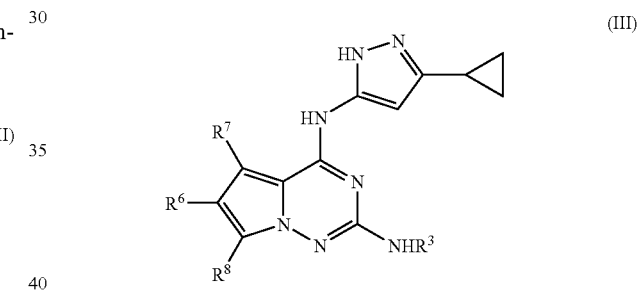

(III)

wherein:

R$^3$ is hydrogen, alkyl, substituted alkyl, cycloalkyl, substituted cycloalkyl, aryl, substituted aryl,

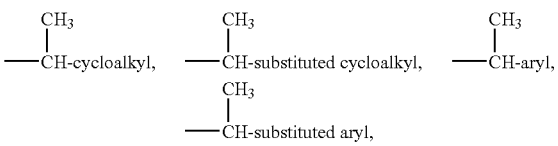

heteroaryl, substituted heteroaryl, heterocyclyl, substituted heterocyclyl, —CONHR$^4$, —CONHSO$_2$R$^4$, —(CH$_2$)$_n$-aryl, —(CH$_2$)$_n$-substituted aryl, —(CH$_2$)$_n$-heteroaryl, —(CH$_2$)$_n$-substituted heteroaryl, —(CHR$^4$)$_n$CONHalkyl, —(CHR$^4$)$_n$CONHsubstituted aryl, —(CHR$^4$)$_n$CONH heteroaryl, —(CHR$^4$)$_n$CONHsubstituted heteroaryl, —(CHR$^4$)$_n$CONH(CH$_2$)$_n$—OH, —(CH$_2$)$_2$(CH$_2$)$_n$—OH, —(CH$_2$)$_2$(CH$_2$)$_n$—NH$_2$ or —(CH$_2$)$_2$(CH$_2$)$_n$—S-alkyl, two of which may be attached to the same ring carbon atom provided that the resultant compound is chemically stable;

R$^4$ is hydrogen, C$_1$-C$_4$ alkyl or phenyl;

R$^6$ and R$^7$ are independently hydrogen, C$_1$-C$_4$ alkyl, halogen, cyano, amino or substituted amino;

$R^8$ is hydrogen, $C_1$-$C_6$ alkyl, $C_1$-$C_6$ alkenyl, $C_1$-$C_6$ alkynyl, $C_3$-$C_8$ cycloalkyl, $C_1$-$C_5$ arylalkyl or $C_4$-$C_8$ heterocyclyl with at least one atom on the ring selected from a nitrogen or oxygen atom, and each of said $R^8$ groups optionally substituted with 1 to 3 groups selected from the group consisting of —OH, $OR^8$, —$NH_2$, —$NR^8R^9$, —$CONHR^8$, —$OCONHR^9$, —$CONHSO_2R^9$, —$NHCONHR^9$, —$SR^9$, —$S(=O)R^9$, —$SO_2R^9$ and —$SO_2N R^9R^{10}$;

$R^9$ is $C_1$-$C_6$ alkyl, $C_3$-$C_6$ cycloalkyl, an optionally substituted aryl or heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

$R^{10}$ is hydrogen, halogen, $C_1$-$C_6$ alkyl, $C_3$-$C_6$ cycloalkyl or $C_1$-$C_6$ alkoxy;

n is 0, 1, 2, 3 or 4;

or a pharmaceutically acceptable salt, tautomer or stereoisomer thereof.

Compounds of the invention include the following:

$N^4$-(3-cyclopropyl-1H-pyrazol-5-yl)-$N^2$-((1S)-1-(4-fluorophenyl)ethyl)pyrrolo[2,1-f][1,2,4]triazine-2,4-diamine, $N^2$-((1S)-1-cyclohexylethyl)-$N^4$-(3-cyclopropyl-1H-pyrazol-5-yl)pyrrolo[2,1-f][1,2,4]triazine-2,4-diamine, $N^2$-(1-benzyl-4-piperidinyl)-$N^4$-(5-cyclopropyl-1H-pyrazol-3-yl)pyrrolo[2,1-f][1,2,4]triazine-2,4-diamine, $N^2$-((3R)-1-benzyl-3-pyrrolidinyl)-$N^4$-(3-cyclopropyl-1H-pyrazol-5-yl)pyrrolo[2,1-f][1,2,4]triazine-2,4-diamine, $N^2$-((3S)-1-benzyl-3-pyrrolidinyl)-$N^4$-(3-cyclopropyl-1H-pyrazol-5-yl)pyrrolo[2,1-f][1,2,4]triazine-2,4-diamine, $N^4$-(5-cyclopropyl-1H-pyrazol-3-yl)-$N^2$-((3S)-1-(1,3-thiazol-2-ylmethyl)-3-pyrrolidinyl)pyrrolo[2,1-f][1,2,4]triazine-2,4-diamine, $N^4$-(3-cyclopropyl-1H-pyrazol-5-yl)-$N^2$-((1S)-1-methylpentyl)pyrrolo[2,1-f][1,2,4]triazine-2,4-diamine, $N^4$-(3-cyclopropyl-1H-pyrazol-5-yl)-$N^2$-(2-(methylsulfanyl)ethyl)pyrrolo[2,1-f][1,2,4]triazine-2,4-diamine, (S)-$N^4$-(3-cyclopropyl-1H-pyrazol-5-yl)-7-(3-(dimethylamino)prop-1-ynyl)-N2-(1-(4-fluorophenyl)ethyl)pyrrolo[1,2-f][1,2,4]triazine-2,4-diamine, $N^2$-((1S)-1-(4-fluorophenyl)ethyl)-$N^4$-(3-phenyl-1H-pyrazol-5-yl)pyrrolo[2,1-f][1,2,4]triazine-2,4-diamine, or a pharmaceutically acceptable salt thereof.

Definitions

The following are definitions of terms that may be used in the present specification. The initial definition provided for a group or term herein applies to that group or term throughout the present specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "arylalkyl" or "aralkyl" refers to an aryl or a substituted aryl group bonded directly through an alkyl group, such as benzyl, wherein the alkyl group may be branched or straight chain. In the case of a "substituted arylalkyl", the Alkyl portion of the group may, besides being branched or straight chain, be substituted as recited above for substituted alkyl groups and the aryl group may be substituted as recited for substituted aryl.

The term "aryloxy" refers to an aryl or a substituted aryl group bonded directly through an alkoxy group, such as methoxy or ethoxy.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle", "heterocyclyl" or "heterocyclic group" is intended to mean a stable 3, 4, 5, 6, or 7-membered monocyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, 4, or 5 ring heteroatoms independently selected from the group consisting of N, O and S. Heterocycle includes any bicyclic group in which one heterocyclic ring is fused to a second ring, which may be carbocyclic (e.g. benzo fusion) or heterocyclic. When a heterocycle is referred to as an "aromatic heterocycle" or "heteroaryl," this means that a fully unsaturated, i.e., aromatic, ring is present in the heterocycle. An aromatic heterocycle only requires one ring to be aromatic, if more than one ring is present. The aromatic portion of the aromatic heterocycle can be a carbocycle or heterocycle. The nitrogen and sulfur heteroatoms in the heterocycle may optionally be oxidized (i.e., N→O and S(O)p). The nitrogen atom may be unsubstituted (i.e., N or NH) or substituted (i.e., NR wherein R is a substituent) and may optionally be quaternized. The heterocyclic ring may be attached to its pendant group at any heteroatom or carbon atom that results in a stable structure. The heterocyclic rings described herein may be substituted on a carbon or on a nitrogen atom, if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. It is to be noted that total number of S and O atoms in the aromatic heterocycle is not more than 1. Bridged and spiro rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro rings are formed when to or more atoms (i.e., C, O, N, or S) of a chain are attached to the same carbon atom of a heterocycle (or carbocycle if fused to a heterocycle). When a spiro ring is present, the substituents recited for the ring may also be present on the spiro. When the term "heterocycle" is used, it is intended to include heteroaryl.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents. Also included are smaller heterocyclyls, such as, epoxides and aziridines.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

In addition, zwitterions ("inner salts") may be formed.

The compounds herein described have asymmetric centers and are shown as being trans-substituted. The trans-substitution pattern shown and its mirror image are both encompassed by the presently claimed invention. In one embodiment, the shown absolute stereochemistry is preferred. In another embodiment, the mirror image of the shown stereochemistry is preferred.

Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs,* edited by H. Bundgaard, (Elsevier, 1985), and *Methods in Enzymology,* Vol. 112, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, pp. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou and Talalay, *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Utility

The present invention is based on the discovery that certain pyrrolotriazines are inhibitors of protein kinases. More specifically, pyrrolotriazines such as those described in this invention inhibit the protein tyrosine kinase activity of members of the TRK family of receptors. These inhibitors will be useful in the treatment of proliferative diseases that are dependent on signaling by one or more of these receptors. Such diseases include solid tumors of the pancreatic, prostate, lung, head and neck, breast, colon, ovary, as well as other tumor types including multiple myeloma, melanoma, neuroblastoma, gliobalstoma and other hematological disorders such as acute myelogenous leukemia. The invention relates to a pharmaceutical composition of compound of formula I, or pharmaceutically acceptable salt or hydrate thereof, and a pharmaceutically acceptable carrier in the treatment of hyperproliferative disorder in mammal. In particular, said pharmaceutical composition is expected to inhibit the growth and/or metastasis of those primary and recurrent solid tumors which are associated with TrkA, TrkB, TrkC, Flt-3 (Fms-like kinase-3) and Tie-2, especially those tumors which are significantly dependent on TrkA, TrkB, TrkC, Flt-3, Tie-2 for their growth and spread, including for example, cancers of the thyroid, breast, colon, pancreas, or a variety of tumor types including multiple myeloma, melanoma, neuroblastoma, glioblastoma and acute myelogenous leukemia.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit TrkA, TrkB, TrkC, Flt-3 and Tie-2 kinases, compounds of the present invention can be used for the treatment of proliferative diseases, including cancer. The TrkA, TrkB and TrkC receptor kinases have been shown to be expressed and activated in tumors including thyroid, breast, colon, acute myelogenous leukemia and elevated Trk receptors and corresponding ligands have also been reported in a variety of tumor types including multiple myeloma, melanoma, pancreatic acnrcinoma, neuroblastoma and glioblastoma. It is therefore expected that inhibitors of the TrkA, TrkB and TrkC kinases will have efficacy in the treatment of tumors that depend on signaling from either or both of the two receptors. These compounds are expected to have efficacy either as single agent or in combination (simultaneous or sequentially) with other chemotherapeutic agents such as Taxol®, adriamycin, and cisplatin.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib (Sprycel®); Casodex® (bicalutamide, Astra Zencca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione(ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adrenocarcinoma, breast, colon, lung, ovary, pancreas, and thyroid;

tumors of the central and peripheral nervous system, including neuroblastoma, glioblastoma, and medulloblastoma; and hematological malignancies such as acute myelogenous leukemia (AML)

other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fme-like kinase-3), Tie-2, CDK2, VEGFR, FGFR and IGFR kinases.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

TrkA

The ability of compounds of the present invention to inhibit tyrosine kinase activity of TrkA may be measured using a recombinant enzyme in an assay that measures the ability of compounds to inhibit the phosphorylation of the exogenous substrate, polyGluTyr (PGT, Sigma™, 4:1). The kinase domain of the human TrkA receptor is expressed in Sf9 insect cells as a histidine (His)-fusion protein using a baculovirus expression system. The protein is purified from the lysates of these cells using an Ni-NTA affinity column. After the recombinant enzyme is purified, it is activated by incubation with cold ATP. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 0.1 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol)(Perkin Elmer™) After a 1 hour incubation at 30° C., the reaction is terminated with 10% TCA and incubated at 4° C. for 1 hour. The reaction is filtered onto a Unifilter® GF/C™ filter plate (Perkin Elmer™) that has been presoaked with 0.1M NaPyrophosphate. Microscint-20 (Perkin Elmer™) is then added to the dried filter plate and the captured $^{33}$P-phosphorylated PGT is quantitated on a microscintillation plate counter (TopCount•NXT™ (Perkin Elmer™)). Inhibition of the kinase enzymatic activity by the test compound is detected by a reduction in scintillation, and the concentration of compound that is required to inhibit the signal by 50% is reported as the $IC_{50}$ value for the test compound.

TrkB

The ability of compounds of the present invention to inhibit tyrosine kinase activity of TrkB may be measured using a recombinant enzyme in an assay that measures the ability of compounds to inhibit the phosphorylation of the exogenous substrate, polyGluTyr (PGT, Sigma™, 4:1). The kinase domain of the human TrkB receptor (amino acids 526-838) is expressed in insect cells as a histidine (His)-fusion protein and is commercially available from Invitrogen™. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 0.1 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol) (Perkin Elmer™). After a 1 hour incubation at 30° C., the reaction is terminated with 10% TCA and incubated at 4° C. for 1 hour. The reaction is filtered onto a Unifilter® GF/C™ filter plate (Perkin Elmer™) that has been presoaked with 0.1M NaPyrophosphate. Microscint-20(Perkin Elmer™) is then added to the dried filter plate and the captured $^{33}$P-phosphorylated PGT is quantitated on a microscintillation plate counter (TopCount•NXT™ (Perkin Elmer™)). Inhibition of the kinase enzymatic activity by the test compound is detected by a reduction in scintillation, and the concentration of compound that is required to inhibit the signal by 50% is reported as the $IC_{50}$ value for the test compound.

The instant compounds inhibit TrkA and TrkB with $IC_{50}$ values between 0.001 to 10 µM. Preferred compounds have $IC_{50}$ values between 0.001-2.5 µM. More preferred compounds have $IC_{50}$ values between 0.001-0.5 µM. Most preferred compounds have $IC_{50}$ values between 0.001-0.1 µM.

Compounds described herein were tested in the TrkA and TrkB assays described above. The following results were obtained.

| Compound | Kinase Activity (IC$_{50}$, µM) | |
|---|---|---|
| | TrkA | TrkB |
| 2 | 0.0001 | 0.0003 |
| 43 | 0.0003 | 0.0003 |
| 38 | 0.0005 | 0.0009 |
| 28 | 0.0007 | 0.0007 |
| 44 | 0.001 | 0.002 |
| 40 | 0.003 | 0.004 |
| 12 | 0.006 | 0.035 |
| 49 | 0.012 | 0.005 |
| 41 | 0.018 | 0.031 |
| 9 | 0.074 | 0.225 |

Abbreviations

The following abbreviations are employed in the methods of preparation and Examples:
h=hours
DCM=dichloromethane
THF=tetrahydrofuran
HPLC=high performance liquid chromatography
DIEA=diisopropylethyl amine
i-PrOH=isopropyl alcohol
TFA=trifluoroacetic acid
min=minutes
DMF=dimethylformamide
EDC=N-(3-Dimethylaminopropyl)N'-ethylcarbodiimide
HOBt=hydroxybenzotriazole
NMP=N-methylpyrolidinone
EtOAc=ethyl acetate
AcOH=acetic acid
BOP reagent=benzotriazole-1-yl-oxy-tris-(dimethylamino)-phasphoniumhexafluorophosphate
brine=saturated aqueous sodium chloride solution
Et$_3$N=triethylamine
t$_R$=retention time Methods of Preparation Certain compounds of formula I may generally be prepared according to the following schemes and the knowledge of one skilled in the art.

Scheme 1 illustrates one route toward compounds of formula I. A suitable dihalo-pyrrolotriazine III may be treated with an appropriately substituted amino pyrazole in a suitable solvent such as isopropanol in the presence of a base such as diisopropylethylamine to afford compounds of general formula IV. The second halogen may be displaced by amines either thermally or under microwave conditions using either the amine or dimethylformamide or dimethylacetamide as solvent in the presence or absence of a transition metal catalyst such as Pd and a corresponding phosphorus based ligand to afford compounds of formula V.

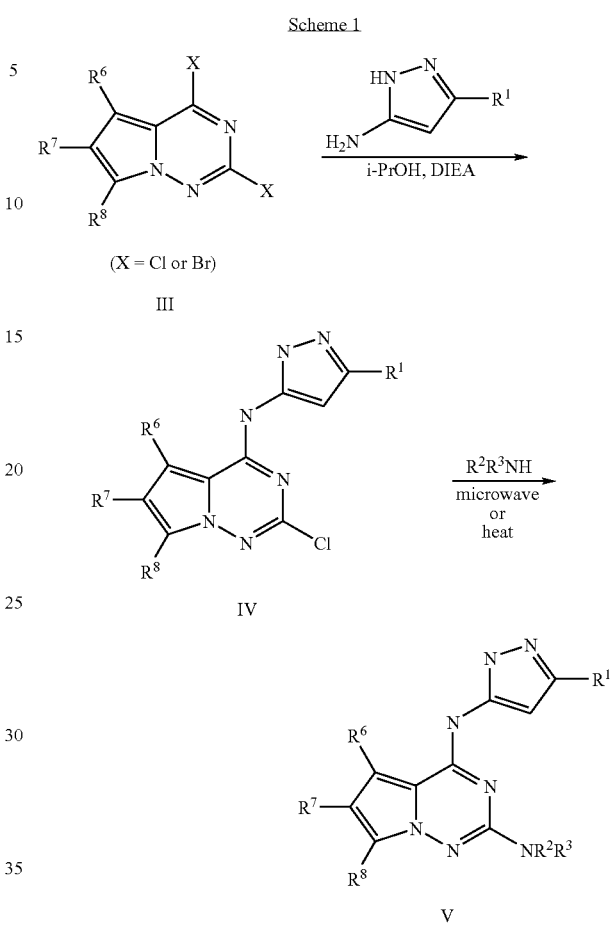

Alternatively, compounds of formula I may be prepared as outlined in Scheme 2. Bis(1-benzotriazoyl)methanethione may be treated with a primary amine followed by 1-amino-2-pyrrole carboxamide to afford thiourea VI. Thiourea VI may be cyclized using a transition metal such as Cu(OAc)$_2$ under basic conditions to afford pyrrolotriazine VII. Treatment with a suitable chlorinating reagent such as POCl$_3$ affords chloroimidate VIII which may be treated with an appropriately substituted amino pyrazole in the presence of an acid such as a boronic acid to afford compounds of formula IX.

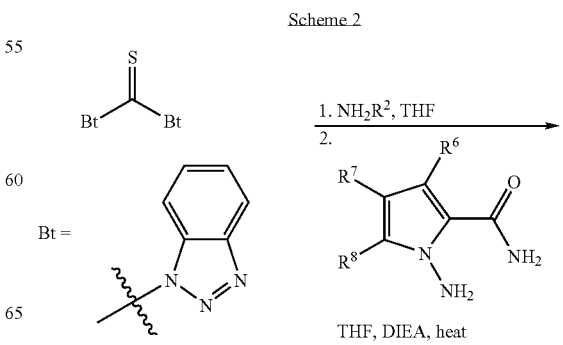

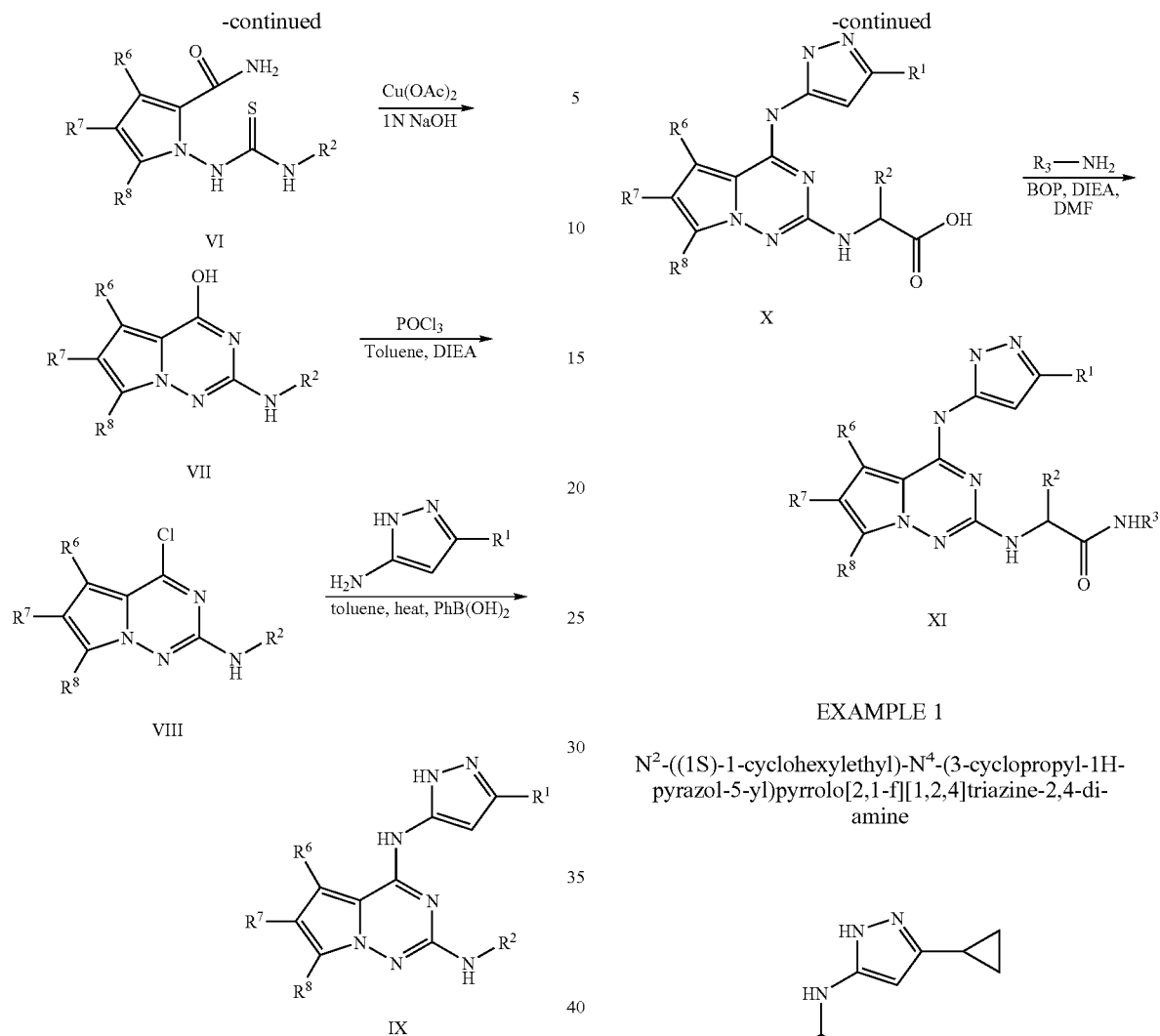

Additionally, compounds of general formula II may be prepared from IV by treatment with the sodium salt of an amino acid in a solvent such as N-methylpyrrolidinone (NMP) at an elevated temperature to afford compounds of formula X. Compounds of formula X may further be elaborated through coupling of amines under standard peptide coupling conditions such as Bop reagent to afford compounds of formula XI.

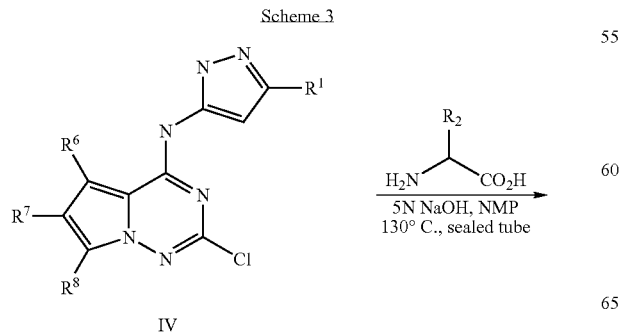

EXAMPLE 1

$N^2$-((1S)-1-cyclohexylethyl)-$N^4$-(3-cyclopropyl-1H-pyrazol-5-yl)pyrrolo[2,1-f][1,2,4]triazine-2,4-diamine

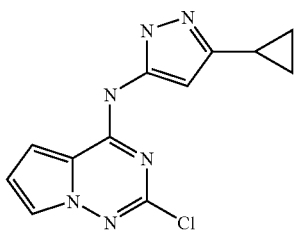

1A. Preparation of 2-chloro-N-(3-cyclopropyl-1H-pyrazol-5-yl)pyrrolo[1,2-f][1,2,4]triazin-4-amine A solution of 2,4-dichloropyrrolo[1,2-f][1,2,4]triazine (1.5 g, 5.3 mmol) in i-PrOH (15 mL) was treated with 3-cyclopropyl-1H-pyrazol-5-amine (657 mg, 5.3 mmol) and DIEA (0.92 mL, 5.3 mmol). The reaction was stirred overnight at ambient temperature and then filtered. The filter cake was washed with cold i-PrOH and dried under vacuum to afford 1A as a solid (1.3 g, 90%). HPLC $t_R$=3.301 min (YMC S5 Combiscreen ODS 4.6×50 mm, 10-90% aqueous methanol containing 0.2% $H_3PO_4$, 4 min gradient, monitored at 254 nm). [M+H]$^+$=275.37.

1B. Preparation of $N^2$-((1S)-1-cyclohexylethyl)-$N^4$-(3-cyclopropyl-1H-pyrazol-5-yl)pyrrolo[2,1-f][1,2,4]triazine-2,4-diamine

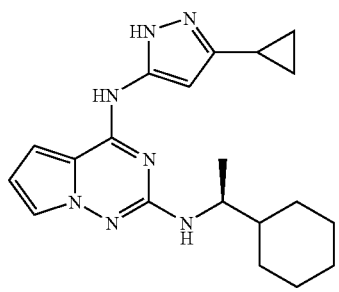

A mixture of 2-chloro-N-(3-cyclopropyl-1H-pyrazol-5-yl) pyrrolo[1,2-f][1,2,4]triazin-4-amine (1A.) (200 mg, 0.74 mmol) and (S)-1-cyclohexylethanamine (0.5 mL) was heated in a microwave safe tube (10 mL) at 120° C. for 60 minutes using 300 W continuous power. The reaction progress was monitored by HPLC. Reaction heated again at 120° C. for 60 minutes using 300 W continuous power, followed by 3 h at 120° C. The reaction was diluted with MeOH (1.5 mL) and purified by preparative reversed-phase HPLC to afford the title compound as a solid (220 mg, 40%). HPLC $t_R$=3.581 min (Chromolith SpeedROD 4.6×50 mm, 10-90% aqueous methanol containing 0.1% TFA, 4 min gradient, monitored at 220 nm). [M+H+]=366.30.

EXAMPLE 2

$N^4$-(3-cyclopropyl-1H-pyrazol-5-yl)-$N^2$-((1S)-1-(4-fluorophenyl)ethyl)pyrrolo[2,1-f][1,2,4]triazine-2,4-diamine

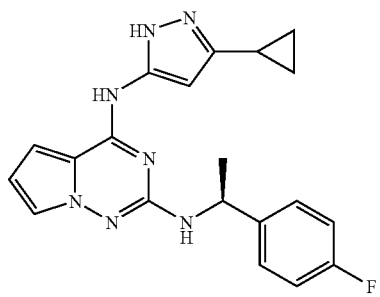

2A. Preparation of (S)-1-(3-(1-(4-fluorophenyl)ethyl)thioureido)-1H-pyrrole-2-carboxamide

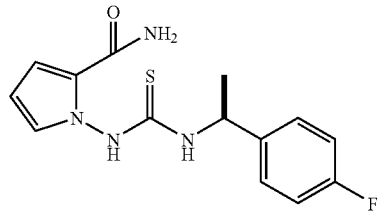

A solution of di(1H-benzo[d][1,2,3]triazol-1-yl)methanethione (3.0 g, 10.7 mmol) in THF (60 mL) was treated with (S)-1-(4-fluorophenyl)ethanamine (1.49 g, 10.7 mmol). The reaction was stirred at ambient temperature for 18 h and then 1-amino-1H-pyrrole-2-carboxamide (1.33 g, 10.7 mmol) was added, followed by triethylamine (2.9 mL, 10.7 mmol). The resulting mixture was warmed to 50° C. and stirred for 16 hours. The reaction mixture was concentrated, then diluted with EtOAc (50 mL) and washed with saturated aqueous $NaHCO_3$ (3×25 mL) and brine (25 mL). The organic layer was dried ($Na_2SO_4$), filtered and concentrated. The crude product was purified by flash chromatography ($SiO_2$, 0% to 2% MeOH/$CH_2Cl_2$ gradient) to afford the desired compound as a solid (2.4 g, 73%). HPLC $t_R$=2.636 min (Combiscreen ODS 4.6×50 mm, 10-90% aqueous methanol containing 0.2% $H_3PO_4$ 4 min gradient, monitored at 220 nm). [M+H+]=307.33.

2B. Preparation of (S)-2-(1-(4-fluorophenyl)ethylamino)pyrrolo[1,2-f][1,2,4]triazin-4-ol

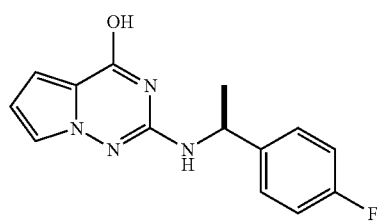

A suspension of 2A (2.4 g, 7.8 mmol) and Cu(OAc)$_2$ $H_2O$ (1.87 g, 9.4 mmol) in 1N NaOH (46.8 mL) was heated to 100° C. for 90 minutes. The reaction was cooled to ambient temperature and filtered through a pad of celite, rinsing with a small amount of cold 1 N NaOH. The filtrate was brought to pH 6 with acetic acid and the resulting solid was filtered and dried under vacuum. The crude product was purified by reversed-phase preparative HPLC (YMC ODS-A 5 uM 30×100 mm, 10-90% aqueous methanol containing 0.1% TFA, 15 min gradient, monitored at 220 nm) to afford the desired as a solid (1.5 g, 71%). HPLC $t_R$=3.128 min (YMC S5 Combiscreen ODS 4.6×50 mm, 10-90% aqueous methanol containing 0.2% $H_3PO_4$, 4 min gradient, monitored at 254 nm). [M+H]$^+$=273.28.

2C. Preparation of (S)-2-(1-(4-fluorophenyl)ethylamino)pyrrolo[1,2-f][1,2,4]triazin-4-ol

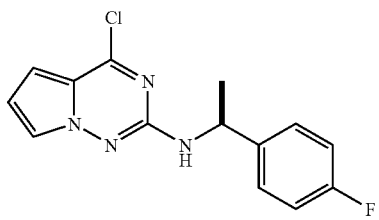

A solution of 2B (200 mg, 0.74 mmol) in toluene (5 mL) was treated with POCl$_3$ (0.082 mL, 0.88 mmol) and DIEA (0.114 mL, 0.67 mmol). The reaction was heated to reflux for 18 hours, then cooled to ambient temperature and poured into ice cold saturated aqueous NaHCO$_3$ (25 mL). The mixture was extracted with EtOAc (3×25 mL), and the combined organics were washed again with saturated aqueous NaHCO$_3$ (25 mL). The organic layer was dried (Na$_2$SO$_4$), filtered and concentrated. The crude chloride was passed through a pad of SiO$_2$ (10% EtOAc/Hexanes) to afford the desired as an oil (210 mg, 98%). HPLC t$_R$=3.816 min (YMC S5 Combiscreen ODS 4.6×50 mm, 10-90% aqueous methanol containing 0.2% H$_3$PO$_4$, 4 min gradient, monitored at 220 nm). [M+H]$^+$=291.24.

2D. Preparation of N$^4$-(3-cyclopropyl-1H-pyrazol-5-yl)-N$^2$-((1S)-1-(4-fluorophenyl)ethyl)pyrrolo[2,1-f][1,2,4]triazine-2,4-diamine

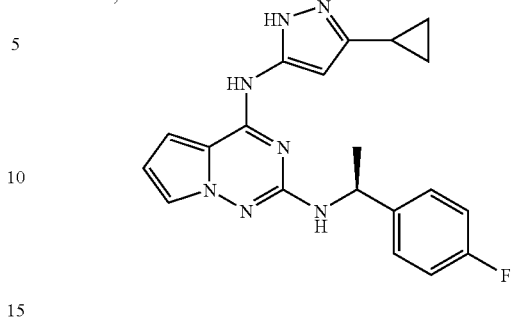

A solution of 2C (100 mg, 0.34 mmol) in toluene (3 mL) was treated with phenylboronic acid (82 mg, 0.52 mmol) and stirred at ambient temperature for one hour. 3-Cyclopropyl-1H-pyrazol-5-amine (209 mg, 1.7 mmol) was added and the reaction was heated to 80° C. for four hours. An additional amount of phenylboronic acid was added (82 mg, 0.52 mmol) and the reaction was heated for 16 hours. More phenylboronic acid was added (82 mg, 0.52 mmol) and the temperature was increased to 90° C. and stirring was continued for 12 hours. The resulting mixture was cooled to ambient temperature and purified by preparative reversed-phase HPLC (YMC ODS-A 5 uM 30×100 mm, 10-90% aqueous methanol containing 0.1% TFA, 30 min gradient, monitored at 220 nm) to afford the title compound (76 mg, 46%). HPLC t$_R$=3.123 min (YMC S5 Combiscreen ODS 4.6×50 mm, 10-90% aqueous methanol containing 0.2% H$_3$PO$_4$, 4 min gradient, monitored at 224 nm). [M+H]+=378.20.

The following compounds in Table 1 have been synthesized utilizing the procedures described in Examples 1 to 2.

TABLE 1

| Ex. No. | R$^1$ | R$^2$ | Compound name | [M + H] | HPLC Ret Time (min) |
|---|---|---|---|---|---|
| 3 | Me | 4-fluorophenethyl | N$^2$-(2-(4-fluorophenyl)ethyl)-N$^4$-(5-methyl-1H-pyrazol-3-yl)pyrrolo[2,1-f][1,2,4]triazine-2,4-diamine | 352 | 1.55$^d$ |
| 4 | Me | 3,4,5-trimethoxyphenyl | N$^4$-(5-methyl-1H-pyrazol-3-yl)-N$^2$-(3,4,5-trimethoxyphenyl)pyrrolo[2,1-f][1,2,4]triazine-2,4-diamine | 396 | 1.605$^d$ |

TABLE 1-continued

| Ex. No. | R¹ | R² | Compound name | [M + H] | HPLC Ret Time (min) |
|---|---|---|---|---|---|
| 5 | Me | phenyl | $N^4$-(5-methyl-1H-pyrazol-3-yl)-$N^2$-phenylpyrrolo[2,1-f][1,2,4]triazine-2,4-diamine | 306 | 1.632$^d$ |
| 6 | cyclopropyl | phenyl | $N^4$-(3-cyclopropyl-1H-pyrazol-5-yl)-$N^2$-phenylpyrrolo[2,1-f][1,2,4]triazine-2,4-diamine | 332 | 2.137$^d$ |
| 7 | Me | -(CH₂)₄NH₂ | $N^2$-(4-aminobutyl)-$N^4$-(5-methyl-1H-pyrazol-3-yl)pyrrolo[2,1-f][1,2,4]triazine-2,4-diamine | 301 | 1.37$^e$ |
| 8 | Me | -(CH₂)₂NH₂ | $N^2$-(2-aminoethyl)-$N^4$-(5-methyl-1H-pyrazol-3-yl)pyrrolo[2,1-f][1,2,4]triazine-2,4-diamine | 273 | 1.26$^e$ |
| 9 | Me | cyclohexyl | $N^2$-cyclohexyl-$N^4$-(5-methyl-1H-pyrazol-3-yl)pyrrolo[2,1-f][1,2,4]triazine-2,4-diamine | 312 | 2.28$^e$ |
| 10 | cyclopropyl | 3-aminobenzyl | $N^2$-(3-aminobenzyl)-$N^4$-(3-cyclopropyl-1H-pyrazol-5-yl)pyrrolo[2,1-f][1,2,4]triazine-2,4-diamine | 361 | 1.163$^d$ |
| 11 | cyclopropyl | 4-aminocyclohexyl | $N^2$-(4-aminocyclohexyl)-$N^4$-(3-cyclopropyl-1H-pyrazol-5-yl)pyrrolo[2,1-f][1,2,4]triazine-2,4-diamine | 353 | 1.222$^d$ |
| 12 | cyclopropyl | 3-aminocyclohexyl | $N^2$-(3-aminocyclohexyl)-$N^4$-(3-cyclopropyl-1H-pyrazol-5-yl)pyrrolo[2,1-f][1,2,4]triazine-2,4-diamine | 353 | 1.218$^d$ |
| 13 | Me | trans-4-aminocyclohexyl | $N^2$-(trans-4-aminocyclohexyl)-$N^4$-(5-methyl-1H-pyrazol-3-yl)pyrolo[2,1-f][1,2,4]triazine-2,4-diamine | 327.1 | 1.967$^c$ |

TABLE 1-continued

| Ex. No. | R$^1$ | R$^2$ | Compound name | [M + H] | HPLC Ret Time (min) |
|---|---|---|---|---|---|
| 14 | cyclopropyl | 2-(3-pyridinyl)ethyl | N$^4$-(3-cyclopropyl-1H-pyrazol-5-yl)-N$^2$-(2-(3-pyridinyl)ethyl)pyrrolo[2,1-f][1,2,4]triazine-2,4-diamine | 361 | 1.087$^d$ |
| 15 | cyclopropyl | 2-(2-pyridinyl)ethyl | N$^4$-(3-cyclopropyl-1H-pyrazol-5-yl)-N$^2$-(2-(2-pyridinyl)ethyl)pyrrolo[2,1-f][1,2,4]triazine-2,4-diamine | 361 | 1.117$^d$ |
| 16 | cyclopropyl | 4-pyridinylmethyl | N$^4$-(3-cyclopropyl-1H-pyrazol-5-yl)-N$^2$-(4-pyridinylmethyl)pyrrolo[2,1-f][1,2,4]triazine-2,4-diamine | 347 | 1.065$^d$ |
| 17 | cyclopropyl | 2-(3-chlorophenyl)ethyl | N$^2$-(2-(3-chlorophenyl)ethyl)-N$^4$-(3-cyclopropyl-1H-pyrazol-5-yl)pyrrolo[2,1-f][1,2,4]triazine-2,4-diamine | 395 | 1.685$^d$ |
| 18 | cyclopropyl | 2-(2-chlorophenyl)ethyl | N$^2$-(2-(2-chlorophenyl)ethyl)-N$^4$-(3-cyclopropyl-1H-pyrazol-5-yl)pyrrolo[2,1-f][1,2,4]triazine-2,4-diamine | 395 | 1.677$^d$ |
| 19 | cyclopropyl | 2-(4-chlorophenyl)ethyl | N$^2$-(2-(4-chlorophenyl)ethyl)-N$^4$-(3-cyclopropyl-1H-pyrazol-5-yl)pyrrolo[2,1-f][1,2,4]triazine-2,4-diamine | 395 | 1.698$^d$ |
| 20 | cyclopropyl | 3-chlorobenzyl | N$^2$-(3-chlorobenzyl)-N$^4$-(3-cyclopropyl-1H-pyrazol-5-yl)pyrrolo[2,1-f][1,2,4]triazine-2,4-diamine | 381 | 1.633$^d$ |
| 21 | cyclopropyl | 4-chlorobenzyl | N$^2$-(4-chlorobenzyl)-N$^4$-(3-cyclopropyl-1H-pyrazol-5-yl)pyrrolo[2,1-f][1,2,4]triazine-2,4-diamine | 381 | 1.647$^d$ |

TABLE 1-continued

| Ex. No. | R¹ | R² | Compound name | [M + H] | HPLC Ret Time (min) |
|---|---|---|---|---|---|
| 23 | cyclopropyl | (S)-1-(4-fluorophenyl)ethyl | N⁴-(3-cyclopropyl-1H-pyrazol-5-yl)-N²-((S)-1-(4-fluorophenyl)ethyl)pyrrolo[2,1-f][1,2,4]triazine-2,4-diamine | 378.2 | 3.123[a] |
| 24 | cyclopropyl | 1-benzyl-4-piperidinyl | N²-(1-benzyl-4-piperidinyl)-N⁴-(5-cyclopropyl-1H-pyrazol-3-yl)pyrrolo[2,1-f][1,2,4]triazine-2,4-diamine | 429 | 2.21[e] |
| 25 | cyclopropyl | (3R)-1-benzyl-3-pyrrolidinyl | N²-((3R)-1-benzyl-3-pyrrolidinyl)-N⁴-(3-cyclopropyl-1H-pyrazol-5-yl)pyrrolo[2,1-f][1,2,4]triazine-2,4-diamine | 415.3 | 2.163[a] |
| 26 | cyclopropyl | (3S)-1-benzyl-3-pyrrolidinyl | N²-((3S)-1-benzyl-3-pyrrolidinyl)-N⁴-(3-cyclopropyl-1H-pyrazol-5-yl)pyrrolo[2,1-f][1,2,4]triazine-2,4-diamine | 415.3 | 2.157[a] |
| 27 | cyclopropyl | (3S)-1-(1,3-thiazol-2-ylmethyl)-3-pyrrolidinyl | N⁴-(5-cyclopropyl-1H-pyrazol-3-yl)-N²-((3S)-1-(1,3-thiazol-2-ylmethyl)-3-pyrrolidinyl)pyrrolo[2,1-f][1,2,4]triazine-2,4-diamine | 442 | 1.98[e] |
| 28 | phenyl | (1S)-1-(4-fluorophenyl)ethyl | N²-((1S)-1-(4-fluorophenyl)ethyl)-N⁴-(3-phenyl-1H-pyrazol-5-yl)pyrrolo[2,1-f][1,2,4]triazine-2,4-diamine | 414.18 | 3.578[a] |
| 29 | C(O)NH₂ | (1S)-1-(4-fluorophenyl)ethyl | 5-((2-(((1S)-1-(4-fluorophenyl)ethyl)amino)pyrrolo[2,1-f][1,2,4]triazin-4-yl)amino)-1H-pyrazole-3-carboxamide | 381.32 | 2.623[b] |
| 30 | cyclopropyl | (1S)-1-methylpentyl | N⁴-(3-cyclopropyl-1H-pyrazol-5-yl)-N²-((1S)-1-methylpentyl)pyrrolo[2,1-f][1,2,4]triazine-2,4-diamine | 340.41 | 3.405[b] |

TABLE 1-continued

| Ex. No. | R¹ | R² | Compound name | [M + H] | HPLC Ret Time (min) |
|---|---|---|---|---|---|
| 31 | 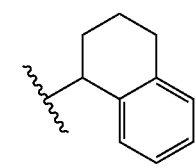 |  | $N^4$-(3-cyclopropyl-1H-pyrazol-5-yl)-$N^2$-(1,2,3,4-tetrahydro-1-naphthalenyl)pyrrolo[2,1-f][1,2,4]triazine-2,4-diamine | 386.36 | 3.426[b] |
| 32 | 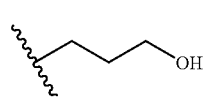 |  | 3-((4-((3-cyclopropyl-1H-pyrazol-5-yl)amino)pyrrolo[2,1-f][1,2,4]triazin-2-yl)amino)-1-propanol | 314.39 | 2.198[a] |
| 33 | 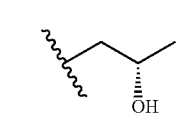 | 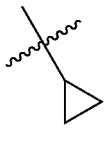 | (2S)-1-((4-((3-cyclopropyl-1H-pyrazol-5-yl)amino)pyrrolo[2,1-f][1,2,4]triazin-2-yl)amino)-2-propanol | 341.43 | 2.297[b] |
| 34 | 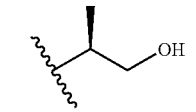 | 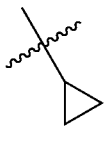 | (2S)-2-((4-((3-cyclopropyl-1H-pyrazol-5-yl)amino)pyrrolo[2,1-f][1,2,4]triazin-2-yl)amino)-1-propanol | 341.43 | 2.264[b] |
| 35 | 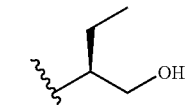 | 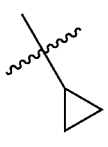 | (2S)-2-((4-((3-cyclopropyl-1H-pyrazol-5-yl)amino)pyrrolo[2,1-f][1,2,4]triazin-2-yl)amino)-1-butanol | 328.32 | 2.483[b] |
| 36 | 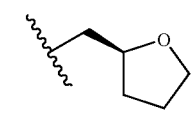 | 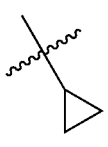 | $N^4$-(3-cyclopropyl-1H-pyrazol-5-yl)-$N^2$-((2S)-tetrahydro-2-furanylmethyl)pyrrolo[2,1-f][1,2,4]triazine-2,4-diamine | 340.34 | 2.590[a] |
| 37 | 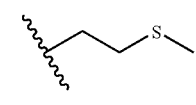 | | $N^4$-(3-cyclopropyl-1H-pyrazol-5-yl)-$N^2$-(2-(methylsulfanyl)ethyl)pyrrolo[2,1-f][1,2,4]triazine-2,4-diamine | 330.25 | 2.693[b] |

TABLE 1-continued

| Ex. No. | R¹ | R² | Compound name | [M + H] | HPLC Ret Time (min) |
|---|---|---|---|---|---|
| 38 | cyclopropyl | trans-4-hydroxycyclohexyl | trans-4-((4-((3-cyclopropyl-1H-pyrazol-5-yl)amino)pyrrolo[2,1-f][1,2,4]triazin-2-yl)amino)cyclohexanol | 354.28 | 2.447[b] |
| 39 | cyclopropyl | (2R)-tetrahydrofuran-2-ylmethyl | $N^4$-(3-cyclopropyl-1H-pyrazol-5-yl)-$N^2$-((2R)-tetrahydro-2-furanylmethyl)pyrrolo[2,1-f][1,2,4]triazine-2,4-diamine | 340.23 | 2.560[b] |
| 40 | cyclopropyl | 2-hydroxybutyl | 1-((4-((3-cyclopropyl-1H-pyrazol-5-yl)amino)pyrrolo[2,1-f][1,2,4]triazin-2-yl)amino)-2-butanol | 328.24 | 2.523[a] |
| 41 | cyclopropyl | (3S)-pyrrolidin-3-yl | $N^4$-(3-cyclopropyl-1H-pyrazol-5-yl)-$N^2$-((3S)-3-pyrrolidinyl)pyrrolo[2,1-f][1,2,4]triazine-2,4-diamine | 325.27 | 1.705[a] |
| 42 | cyclopropyl | (3R)-pyrrolidin-3-yl | $N^4$-(3-cyclopropyl-1H-pyrazol-5-yl)-$N^2$-((3R)-3-pyrrolidinyl)pyrrolo[2,1-f][1,2,4]triazine-2,4-diamine | 325.26 | 1.778[b] |

HPLC Conditions:

(a) YMC S5 Combiscreen ODS 4.6×50 mm, 10-90% aqueous methanol containing 0.2% $H_3PO_4$, 4 min gradient, monitored at 220 or 254 nm (b) Chromolith SpeedROD 4.6×50 mm, 10-90% aqueous methanol containing 0.1% TFA, 4 min gradient, monitored at 220 or 254 nm (c) YMC 4.6×50 mm, 10-90% aqueous methanol containing 0.1% TFA, 4 min gradient, monitored at 220 or 254 nm (d) Phenomenex-luna S10 3.0×50 mm, 10-90% aqueous methanol containing 0.2% $H_3PO_4$, 2 min gradient, monitored at 220 or 254 nm (e) Phenomenex-luna S10 4.6×50 mm, 10-90% aqueous methanol containing 0.2% $H_3PO_4$, 3 min gradient, monitored at 220 or 254 nm

EXAMPLE 43

2-((4-((3-cyclopropyl-1H-pyrazol-5-yl)amino)pyrrolo[2,1-f][1,2,4]triazin-2-yl)amino)-N-1,3-thiazol-2-ylacetamide

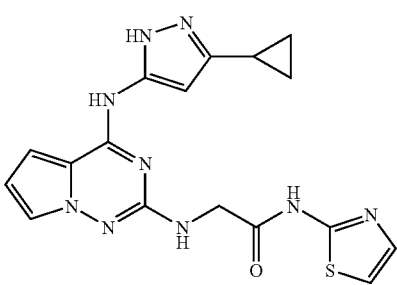

43A. Preparation of 2-chloro-N-(3-cyclopropyl-1H-pyrazol-5-yl)pyrrolo[1,2-f][1,2,4]triazin-4-amine

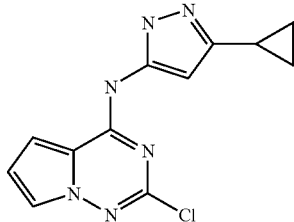

A solution of 2,4-dichloropyrrolo[1,2-f][1,2,4]triazine (1.5 g, 5.3 mmol) in i-PrOH (15 mL) was treated with 3-cyclopropyl-1H-pyrazol-5-amine (657 mg, 5.3 mmol) and DIEA (0.92 mL, 5.3 mmol). The reaction was stirred overnight at ambient temperature and then filtered. The filter cake was washed with cold i-PrOH and dried under vacuum to afford 43A as a solid (1.3 g, 90%). HPLC $t_R$=3.301 min (YMC S5 Combiscreen ODS 4.6×50 mm, 10-90% aqueous methanol containing 0.2% $H_3PO_4$, 4 min gradient, monitored at 254 nm). [M+H]$^+$=275.37.

43B. Preparation of ((4-((3-cyclopropyl-1H-pyrazol-5-yl)amino)pyrrolo[2,1-f][1,2,4]triazin-2-yl)amino)acetic acid

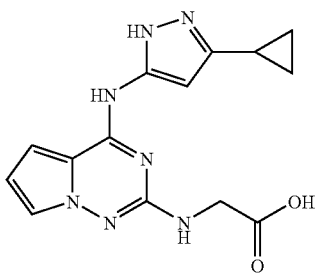

A solution of glycine (268 mg, 3.58 mmol) in 5 N NaOH (0.66 mL, 3.31 mmol) was added to a solution of 2-chloro-N-(3-cyclopropyl-1H-pyrazol-5-yl)pyrrolo[1,2-f][1,2,4]triazin-4-amine (100 mg, 0.36 mmol) in NMP (3 mL). The reaction was capped and heated to 130° C. in a sealed tube for five days. The reaction was cooled to ambient temperature and triturated with water (10 mL). The resulting solid was removed by filtration and the filtrate was acidified to pH 4 with AcOH. The resulting solid was collected by filtration and purified by preparative reversed-phase HPLC to afford the desired acid (10 mg, 11%). HPLC $t_R$=2.168 min (YMC S5 Combiscreen ODS 4.6×50 mm, 10-90% aqueous methanol containing 0.2% $H_3PO_4$, 4 min gradient, monitored at 254 nm). [M+H]+=314.24.

43C. 2-((4-((3-cyclopropyl-1H-pyrazol-5-yl)amino)pyrrolo[2,1-f][1,2,4]triazin-2-yl)amino)-N-1,3-thiazol-2-ylacetamide

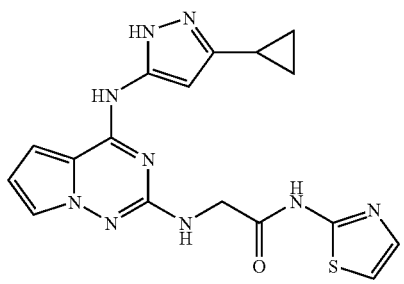

A solution of 43B (8 mg, 0.026 mmol) in DMF (1 mL) was treated with 2-aminothiazole (13 mg, 0.13 mmol) and DIEA (0.01 mL, 0.051 mmol) and BOP reagent (23 mg, 0.051 mmol). The reaction was stirred at ambient temperature for 2 hours and diluted with EtOAc (2 mL). The reaction was washed with 10% aqueous LiCl (3×2 mL), and then saturated aqueous $NaHCO_3$ (1×2 mL). The organic layer was dried ($Na_2SO_4$), filtered and concentrated. The crude reaction was dissolved in MeOH (1 mL) and treated with 1 N NaOH (1 mL) to hydrolyze any dimer. The resulting mixture was concentrated and purified by reversed-phase HPLC to afford the title compound (1.2 mg, 12%). HPLC $t_R$=2.418 min (YMC S5 Combiscreen ODS 4.6×50 mm, 10-90% aqueous methanol containing 0.2% $H_3PO_4$, 4 min gradient, monitored at 254 nm). [M+H]+=396.12.

The following compounds in Table 2 have been synthesized utilizing the procedures described in Example 43.

TABLE 2

| Ex. No. | $R^1$ | $R^2$ | Compound name | [M + H] | HPLC Ret Time (min) |
|---|---|---|---|---|---|
| 44 | (S)-CH$_2$Ph | thiazol-2-yl | (2S)-2-((4-((5-cyclopropyl-1H-pyrazol-3-yl)amino)pyrrolo[2,1-f][1,2,4]triazin-2-yl)amino)-3-phenyl-N-1,3-thiazol-2-ylpropanamide | 486 | 1.59[b] |

TABLE 2-continued

| Ex. No. | R¹ | R² | Compound name | [M + H] | HPLC Ret Time (min) |
|---|---|---|---|---|---|
| 45 | (S)-CH₂Ph | [5-(6-fluoropyridin-2-yl)] | (2S)-2-((4-((5-cyclopropyl-1H-pyrazol-3-yl)amino)pyrrolo[2,1-f][1,2,4]triazin-2-yl)amino)-N-(6-fluoro-3-pyridinyl)-3-phenylpropanamide | 498 | 1.59[b] |
| 46 | H | CH₂C(CH₃)₃ | 2-((4-((3-cyclopropyl-1H-pyrazol-5-yl)amino)pyrrolo[2,1-f][1,2,4]triazin-2-yl)amino)-N-(2,2-dimethylpropyl)acetamide | 383.22 | 2.685[a] |
| 47 | H | [(1R)-1-(hydroxymethyl)-2-methylpropyl] | 2-((4-((3-cyclopropyl-1H-pyrazol-5-yl)amino)pyrrolo[2,1-f][1,2,4]triazin-2-yl)amino)-N-((1R)-1-(hydroxymethyl)-2-methylpropyl)acetamide | 399.22 | 2.332[a] |
| 48 | (S)-Me | CH₂C(CH₃)₃ | (2S)-2-((4-((3-cyclopropyl-1H-pyrazol-5-yl)amino)pyrrolo[2,1-f][1,2,4]triazin-2-yl)amino)-N-(2,2-dimethylpropyl)propanamide | 397.33 | 2.696[a] |
| 49 | (S)-Me | [(1R)-1-(hydroxymethyl)-2-methylpropyl] | (2S)-2-((4-((3-cyclopropyl-1H-pyrazol-5-yl)amino)pyrrolo[2,1-f][1,2,4]triazin-2-yl)amino)-N-((1R)-1-(hydroxymethyl)-2-methylpropyl)propanamide | 413.29 | 2.398[a] |

HPLC Conditions:

(a) YMC S5 Combiscreen ODS 4.6×50 mm, 10-90% aqueous methanol containing 0.2% H₃PO₄, 4 min gradient, monitored at 220 or 254 nm)

(b) PhenomenexC18 10 u 3.0×50 mm, gradient from 10% MeOH-90% water-0.1% TFA to 90% MeOH-10% water-0.1% TFA during 2 minutes.

EXAMPLE 50

(S)-N⁴-(3-cyclopropyl-1H-pyrazol-5-yl)-7-(3-(dimethylamino)prop-1-ynyl)-N²-(1-(4-fluorophenyl)ethyl)pyrrolo[1,2-f][1,2,4]triazine-2,4-diamine

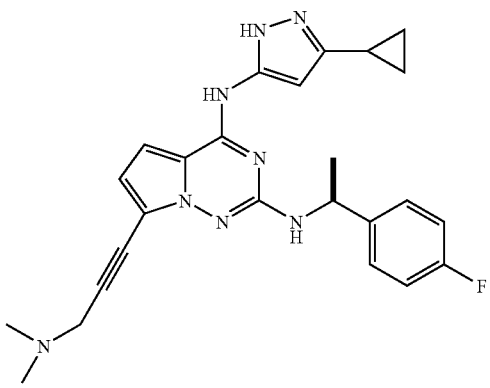

50A. Preparation of (S)-7-bromo-4-chloro-N-(1-(4-fluorophenyl)ethyl)pyrrolo[1,2-f][1,2,4]triazin-2-amine

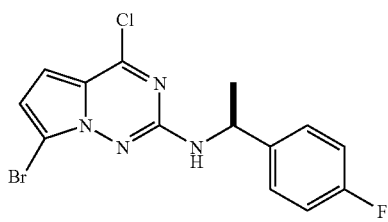

A solution of 2C (155 mg, 0.53 mmol) in acetonitrile (4 mL) was cooled to 0° C. and treated with N-bromosuccinimide (90 mg, 0.5 mmol). The reaction was warmed to room temperature for one hour and then concentrated. The residue was dissolved in EtOAc (25 mL) and washed with water (2×25 mL), brine (25 mL) and dried (Na₂SO₄) before filtering and concentrating under reduced pressure. The crude product was purified by flash chromatography (SiO₂, 40 g column, 0% to 5% EtOAc/Hexanes, 30 minute gradient) to afford the mono-bromo product (130 mg, 67%).

50B. Preparation of (S)-7-bromo-N⁴-(3-cyclopropyl-1H-pyrazol-5-yl)-N²-(1-(4-fluorophenyl)ethyl)pyrrolo[1,2-f][1,2,4]triazine-2,4-diamine

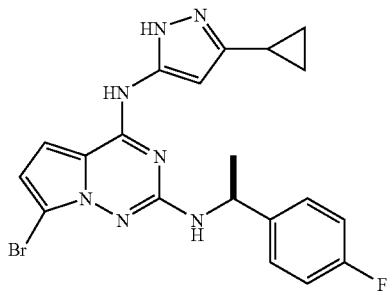

A suspension of 50A (130 mg, 0.35 mmol) in toluene (5 mL) was treated with 3-cyclopropyl-1H-pyrazol-5-amine (217 mg, 1.77 mmol) and phenyl boronic acid (281 mg, 1.77 mmol). The reaction mixture was heated to 90° C. for 24 hours. The resulting suspension was poured into EtOAc (25 mL) and washed with water (25 mL) and saturated aqueous NaHCO₃ (2×25 mL). The organic layer was dried (Na₂SO₄), filter and concentrated. The crude product was purified by preparative reversed-phase chromatography to afford the desired product. HPLC $t_R$=3.585 min (YMC S5 Combiscreen ODS 4.6×50 mm, 10-90% aqueous methanol containing 0.2% H₃PO₄, 4 min gradient, monitored at 254 nm). [M+H]+=456.12.

50C. Preparation of (S)-N⁴-(3-cyclopropyl-1H-pyrazol-5-yl)-7-(3-(dimethylamino)prop-1-ynyl)-N²-(1-(4-fluorophenyl)ethyl)pyrrolo[1,2-f][1,2,4]triazine-2,4-diamine

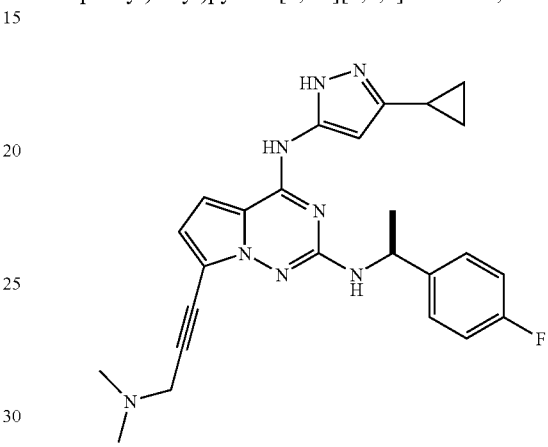

A suspension of 50B (40 mg, 0.09 mmol) in THF (2 mL) and Et₃N (0.75 mL) was treated with Pd(dppf)₂Cl₂ (7 mg), CuI (3 mg, 0.018 mmol) and N,N-dimethyl propargylamine (0.047 mL, 0.44 mmol). The reaction mixture was purged with argon and heated to 70° C. for 16 hours. The resulting solution was filtered and concentrated. The crude product was purified by preparative reversed-phase chromatography to afford the desired product. HPLC tR=2.590 min (YMC S5 Combiscreen ODS 4.6×50 mm, 10-90% aqueous methanol containing 0.2% H₃PO₄, 4 min gradient, monitored at 254 nm). [M+H]+=459.21.

We claim:
1. A compound of the formula I

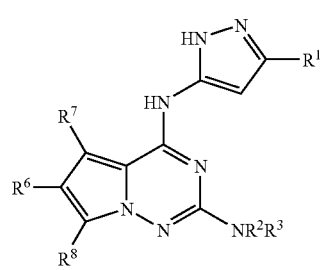

(I)

wherein:
R¹ is alkyl, substituted alkyl, cycloalkyl, substituted cycloalkyl, aryl, substituted aryl or —CONR⁴R⁵;
R² is hydrogen or C₁-C₄ alkyl;
R³ is hydrogen, alkyl, substituted alkyl, cycloalkyl, substituted cycloalkyl, aryl, substituted aryl,

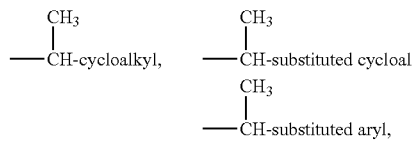

heteroaryl, substituted heteroaryl, heterocyclyl, substituted heterocyclyl, —CONHR$^4$, —CONHSO$_2$R$^4$, —(CH$_2$)$_n$-aryl, —(CH$_2$)$_n$-substituted aryl, —(CH$_2$)$_n$-heteroaryl, —(CH$_2$)$_n$-substituted heteroaryl, —(CHR$^4$)$_n$CONHalkyl, —(CHR$^4$)$_n$CONHsubstituted aryl, —(CHR$^4$)$_n$CONH heteroaryl, —(CHR$^4$)$_n$CONH-substituted heteroaryl, —(CHR$^4$)$_n$CONH(CH$_2$)$_n$—OH, —(CH$_2$)$_2$(CH$_2$)$_n$—OH, —(CH$_2$)$_2$(CH$_2$)$_n$—NH$_2$ or —(CH$_2$)$_2$(CH$_2$)$_n$—S-alkyl, two of which may be attached to the same ring carbon atom;

R$^4$ and R$^5$ are independently hydrogen, C$_1$-C$_4$ alkyl or phenyl;

R$^6$ and R$^7$ are independently hydrogen, C$_1$-C$_4$ alkyl, halogen, cyano, amino or substituted amino;

R$^8$ is hydrogen, C$_1$-C$_6$ alkyl, C$_1$-C$_6$ alkenyl, C$_1$-C$_6$ alkynyl, C$_3$-C$_8$ cycloalkyl, C$_1$-C$_5$ arylalkyl or C$_4$-C$_8$ heterocyclyl with at least one atom on the ring selected from a nitrogen or oxygen atom, and each of said R$^8$ groups optionally substituted with 1 to 3 groups selected from the group consisting of —OH, OR$^9$, —NH$_2$, —NR$^9$R$^{10}$, —CONHR$^9$, —OCONHR$^9$, —CONHSO$_2$R$^9$, —NH-CONHR$^9$, —SR$^9$, —S(=O)R$^9$, —SO$_2$R$^9$ and —SO$_2$NR$^9$R$^{10}$;

R$^9$ is C$_1$-C$_6$ alkyl, C$_3$-C$_6$ cycloalkyl, an optionally substituted aryl or heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

R$^{10}$ is hydrogen, halogen, C$_1$-C$_6$ alkyl, C$_1$-C$_6$ cycloalkyl or C$_1$-C$_6$ alkoxy;

n is 0, 1, 2, 3 or 4;

or a pharmaceutically acceptable salt, tautomer or stereoisomer thereof.

2. The compound according to claim 1 of the formula

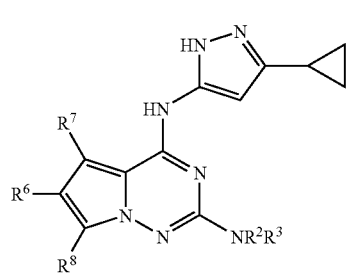

(II)

wherein:

R$^2$ is hydrogen or C$_1$-C$_4$ alkyl;

R$^3$ is hydrogen, alkyl, substituted alkyl, cycloalkyl, substituted cycloalkyl, aryl, substituted aryl, heteroaryl, substituted heteroaryl, heterocyclyl, substituted heterocyclyl, —CONHR$^4$, —CONHSO$_2$R$^4$, —(CH$_2$)$_n$-aryl, —(CH$_2$)$_n$-substituted aryl, —(CH$_2$)$_n$-heteroaryl, —(CH$_2$)$_n$-substituted heteroaryl, —(CHR$^4$)$_n$CONHalkyl, —(CHR$^4$)$_n$CONHsubstituted aryl, —(CHR$^4$)$_n$CONH heteroaryl, —(CHR$^4$)$_n$CONH-substituted heteroaryl, —(CHR$^4$)$_n$CONH(CH$_2$)$_n$—OH, —(CH$_2$)$_2$(CH$_2$)$_n$—OH, —(CH$_2$)$_2$(CH$_2$)$_n$—NH$_2$ or —(CH$_2$)$_2$(CH$_2$)$_n$S-alkyl, two of which may be attached the same ring carbon atom;

R$^4$ is hydrogen, C$_1$-C$_4$ alkyl or phenyl;

R$^6$ and R$^7$ are independently hydrogen, C$_1$-C$_4$ alkyl, halogen, cyano, amino or substituted amino;

R$^8$ is hydrogen, C$_1$-C$_6$ alkyl, C$_1$-C$_6$ alkenyl, C$_1$-C$_6$ alkynyl, C$_3$-C$_8$ cycloalkyl, C$_1$-C$_5$ arylalkyl or C$_4$-C$_8$ heterocyclyl with at least one atom on the ring selected from a nitrogen or oxygen atom, and each of said R$^8$ groups optionally substituted with 1 to 3 groups selected from the group consisting of —OH, OR$^9$, —NH$_2$, —NR$^9$R$^{10}$, —CONHR$^9$, —OCONHR$^9$, —CONHSO$_2$R$^9$, —NH-CONHR$^9$, —SR$^9$, —S(=O)R$^9$, —SO$_2$R$^9$ and —SO$_2$NR$^9$R$^{10}$;

R$^9$ is C$_1$-C$_6$ alkyl, C$_3$-C$_6$ cycloalkyl, an optionally substituted aryl or heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

R$^{10}$ is hydrogen, halogen, C$_1$-C$_6$ alkyl, C$_3$-C$_6$ cycloalkyl or C$_1$-C$_6$ alkoxy;

n is 0, 1, 2, 3 or 4;

or a pharmaceutically acceptable salt, tautomer or stereoisomer thereof.

3. The compound according to claim 1 of the formula

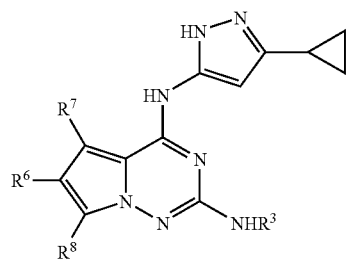

(III)

wherein:

R$^3$ is hydrogen, alkyl, substituted alkyl, cycloalkyl, substituted cycloalkyl, aryl, substituted aryl,

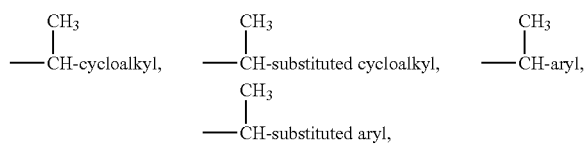

heteroaryl, substituted heteroaryl, heterocyclyl, substituted heterocyclyl, —CONHR$^4$, —CONHSO$_2$R$^4$, —(CH$_2$)$_n$-aryl, —(CH$_2$)$_n$-substituted aryl, —(CH$_2$)$_n$-heteroaryl, —(CH$_2$)$_n$-substituted heteroaryl, —(CHR$^4$)$_n$CONHalkyl, —(CHR$^4$)$_n$CONHsubstituted aryl, —(CHR$^4$)$_n$CONH heteroaryl, —(CHR$^4$)$_n$CONHsubstituted heteroaryl, —(CHR$^4$)$_n$CONH(CH$_2$)$_n$—OH, —(CH$_2$)$_2$(CH$_2$)$_n$—OH, —(CH$_2$)$_2$(CH$_2$)$_n$—NH$_2$ or —(CH$_2$)$_2$(CH$_2$)$_n$—S-alkyl, two of which may be attached to the same ring carbon atom;

R$^4$ is hydrogen, C$_1$-C$_4$ alkyl or phenyl;

R$^6$ and R$^7$ are independently hydrogen, C$_1$-C$_4$ alkyl, halogen, cyano, amino or substituted amino;

R$^8$ is hydrogen, C$_1$-C$_6$ alkyl, C$_1$-C$_6$ alkenyl, C$_1$-C$_6$ alkynyl, C$_3$-C$_8$ cycloalkyl, C$_1$-C$_5$ arylalkyl or C$_4$-C$_8$ heterocyclyl with at least one atom on the ring selected from a nitrogen or oxygen atom, and each of said R$^8$ groups optionally substituted with 1 to 3 groups selected from the group consisting of —OH, OR$^8$, —NH$_2$, —NR$^8$R$^9$, —CONHR$^8$, —OCONHR$^9$, —CONHSO$_2$R$^9$, —NH-CONHR$^9$, —SR$^9$, —S(=O)R$^9$, —SO$_2$R$^9$ and —SO$_2$NR$^9$R$^{10}$;

R$^9$ is C$_1$-C$_6$ alkyl, C$_3$-C$_6$ cycloalkyl, an optionally substituted aryl or heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

R$^{10}$ is hydrogen, halogen, C$_1$-C$_6$ alkyl, C$_3$-C$_6$ cycloalkyl or C$_1$-C$_6$ alkoxy;

n is 0, 1, 2, 3 or 4;

or a pharmaceutically acceptable salt, tautomer or stereoisomer thereof.

4. A compound selected from the group consisting of:

N$^4$-(3-cyclopropyl-1H-pyrazol-5-yl)-N$^2$-((1 S)-1-(4-fluorophenyl)ethyl)pyrrolo[2,1-f][1,2,4]triazine-2,4-diamine, N$^2$-((1S)-1-cyclohexylethyl)-N$^4$-(3-cyclopropyl-1H-pyrazol-5-yl)pyrrolo[2,1-f][1,2,4]triazine-2,4-diamine, N$^2$-(1-benzyl-4-piperidinyl)-N$^4$-(5-cyclopropyl-1H-pyrazol-3-yl)pyrrolo[2,1-f][1,2,4]triazine-2,4-diamine, N$^2$-((3R)-1-benzyl-3-pyrrolidinyl)-N$^4$-(3-cyclopropyl-1H-pyrazol-5-yl)pyrrolo[2,1-f][1,2,4]triazine-2,4-diamine, N$^2$-((3S)-1-benzyl-3-pyrrolidinyl)-N$^4$-(3-cyclopropyl-1H-pyrazol-5-yl)pyrrolo[2,1-f][1,2,4]triazine-2,4-diamine, N$^4$-(5-cyclopropyl-1H-pyrazol-3-yl)-N$^2$-((3 S)-1-(1,3-thiazol-2-ylmethyl)-3-pyrrolidinyl)pyrrolo[2,1-f][1,2,4]triazine-2,4-diamine, N$^4$-(3-cyclopropyl-1H-pyrazol-5-yl)-N$^2$-((1S)-1-methylpentyl)pyrrolo[2,1-f][1,2,4]triazine-2,4-diamine, N$^4$-(3-cyclopropyl-1H-pyrazol-5-yl)-N$^2$-(2-(methylsulfanyl)ethyl)pyrrolo[2,1-f][1,2,4]triazine-2,4-diamine, (S)—N$^4$-(3-cyclopropyl-1H-pyrazol-5-yl)-7-(3-(dimethylamino)prop-1-ynyl)-N2-(1-(4-fluorophenyl)ethyl)pyrrolo[1,2-f][1,2,4]triazine-2,4-diamine, N$^2$-((1S)-1-(4-fluorophenyl)ethyl)-N$^4$-(3-phenyl-1H-pyrazol-5-yl)pyrrolo[2,1-f][1,2,4]triazine-2,4-diamine, or a pharmaceutically acceptable salt thereof.

5. A pharmaceutical composition comprising one or more compounds of claim 1 and a pharmaceutically acceptable carrier.

6. A pharmaceutical composition comprising one or more compounds of claim 2 and a pharmaceutically acceptable carrier.

7. A pharmaceutical composition comprising one or more compounds of claim 3 and a pharmaceutically acceptable carrier.

8. A pharmaceutical composition comprising one or more compounds of claim 4 and a pharmaceutically acceptable carrier.

9. A pharmaceutical composition comprising one or more compounds according to claim 1 in combination with a pharmaceutically acceptable carrier and one or more other anticancer or cytotoxic agent.

10. A method for treating a proliferative disease selected from rheumatoid arthritis and breast cancer, comprising administering to a mammalian species in need thereof, a therapeutically effective amount of one or more compounds according to claim 1.

11. The method for treating a proliferative disease selected from rheumatoid arthritis and breast cancer, farther comprising administering to a mammalian species in need thereof, a therapeutically effective amount of one or more other anticancer or cytotoxic agent in combination with one or more compound according to claim 1.

* * * * *

UNITED STATES PATENT AND TRADEMARK OFFICE
CERTIFICATE OF CORRECTION

| | | |
|---|---|---|
| PATENT NO. | : 7,605,160 B2 | Page 1 of 1 |
| APPLICATION NO. | : 11/835469 | |
| DATED | : October 20, 2009 | |
| INVENTOR(S) | : Fink et al. | |

It is certified that error appears in the above-identified patent and that said Letters Patent is hereby corrected as shown below:

In Column 41, Line 16, Claim 1:
Delete "$CONH(CH_2)_n$," and insert -- $CONH(CH_2)_n$ --

In Column 41, Line 43, Claim 1:
Delete "$C_1-C_6$" and insert -- $C_3-C_6$ --

In Column 42, Line 19, Claim 2:
Delete "—$(CH_2)_2(CH_2)_n$S-alkyl, two of which may be attached" and
insert -- —$(CH_2)_2(CH2)_n$-S-alkyl, two of which may be attached to --

In Column 43, Line 45, Claim 4:
Delete "((1 S)" and insert -- ((1S) --

In Column 44, Line 9, Claim 4:
Delete "((3 S)" and insert -- ((3S) --

In Column 44, Line 44, Claim 11:
Delete "farther" and insert -- further --

Signed and Sealed this
Twenty-sixth Day of April, 2011

David J. Kappos
*Director of the United States Patent and Trademark Office*